US008846048B2

(12) United States Patent
Stiles et al.

(10) Patent No.: US 8,846,048 B2
(45) Date of Patent: *Sep. 30, 2014

(54) COMPOSITIONS AND METHODS FOR DIAGNOSIS, PROGNOSIS AND MANAGEMENT OF MALARIA

(71) Applicant: Morehouse School of Medicine, Atlanta, GA (US)

(72) Inventors: Jonathan K. Stiles, Powder Springs, GA (US); James W. Lillard, Smyrna, GA (US); Henry Benjamin Armatei Armah, Mount Pleasant, MI (US); Nana Otoo Wilson, Atlanta, GA (US)

(73) Assignee: Morehouse School of Medicine, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/721,423

(22) Filed: Dec. 20, 2012

(65) Prior Publication Data

US 2013/0108647 A1  May 2, 2013

Related U.S. Application Data

(63) Continuation of application No. 12/959,043, filed on Dec. 2, 2010, now Pat. No. 8,367,350, and a continuation-in-part of application No. 12/453,079, filed on Apr. 29, 2009, now abandoned.

(51) Int. Cl.
*A61K 39/395* (2006.01)
(52) U.S. Cl.
USPC ..................................................... 424/158.1
(58) Field of Classification Search
None
See application file for complete search history.

(56) References Cited

U.S. PATENT DOCUMENTS

| 4,816,567 A | 3/1989 | Cabilly et al. |
| 2010/0015655 A1 | 1/2010 | Adamczyk et al. |
| 2010/0279319 A1 | 11/2010 | Stiles |

FOREIGN PATENT DOCUMENTS

| WO | 89/01785 | 9/1989 |
| WO | 02/44321 | 6/2002 |
| WO | 2006/116688 A2 | 11/2006 |

OTHER PUBLICATIONS

McMorran et al. (Science, 338:1348-1351, 2012).*
Nandakumar et al. (Antimicrob. Agents Chemo., 50:1859-1860, 2006).*
Akobeng, "Understanding diagnostic tests 3: receiver operating characteristic curves", Acta Paediatrica, 2007, pp. 644-647, vol. 96.
Campanella et al., "Chemokine receptor CXCR3 and its ligands CXCL9 and CXCL10 are required for the development of murine cerebral malaria", Proceedings of the National Academy of Sciences, Mar. 25, 2008, pp. 4814-4819, vol. 105-No. 12.
Hansen et al., "NK Cells Stimulate Recruitment of CXCR3+ T Cells to the Brain during Plasmodium berghei-Mediated Cerebral Malaria", The Journal of Immunology, May 1, 2007, pp. 5779-5788, vol. 178.
Jain et al., "Macrophage migration inhibitory factor is associated with mortality in cerebral malaria patients in India", BMC Research Notes, Mar. 6, 2009, vol. 2-No. 36.
Jain et al., "Burden of Cerebral Malaria in Central India (2004-2007)", American Journal of Tropical Medicine and Hygiene, 2008, pp. 636-642, vol. 79-No. 4.
Marsh et al. "Indicators of Life-Threatening Malaria in African Children", The New England Journal of Medicine, May 25, 1995, pp. 1399-1404, vol. 332-No. 21.
Morrison et al., "Chimeric human antibody molecules: Mouse antigen-binding domains with human constant region domains", Proceedings of the National Academy of Sciences USA, Nov. 1984, pp. 6851-6855, vol. 81.
"Remington: The Science and Practice of Pharmacy vol. II", ed. A.R. Gennaro, 1995, Table of Contents only, Mark Publishing Company, Easton, PA.
World Health Organization, Communicable Diseases Cluster, "Severe falciparum malaria", Transactions of the Royal Society of Tropical Medicine and Hygiene, 2000, pp. S1/1-S1/90, vol. 94-Supplement I.
Altman et al., "Diagnostic tests 3: receiver operating characteristic plots", BMJ, Jul. 16, 1994, pp. 188, vol. 309.
Armah et al., "Cerebrospinal fluid and serum biomarkers of cerebral malaria mortality in Ghanaian children", Malaria Journal, Nov. 12, 2007, pp. 1-17, vol. 6-No. 147.
Jain et al. "Plasma IP-10, apoptotic and angiogenic factors associated with fatal cerebral malaria in India", Malaria Journal, May 19, 2008, pp. 1-15, vol. 7-No. 83.
Sharma, "Re-emergence of malaria in India", Indian Journal of Medical Research, Jan. 1996, pp. 26-45, vol. 103.
Wilson et al.. "Short Report: Detection of Plasmodium falciparum Histidine-rich Protein II in Saliva of Malaria Patients", American Journal of Tropical Medicine and Hygiene, 2008, pp. 733-735, vol. 78-No. 5.
"Malaria Ag Celisa", Cellabs, 2005.
International Search Report and Written Opinion of the International Searching Authority, mailed Jun. 12, 2012 (PCT Application No. PCT/US2011/043058, filed Jul. 6, 2011).

(Continued)

*Primary Examiner* — Brian J Gangle
(74) *Attorney, Agent, or Firm* — Ping Wang; Andrews Kurth LLP

(57) ABSTRACT

Biomarkers for predicting the severity of malaria and methods for their detection are disclosed. In one aspect, the present application discloses CXCL4, CXCL10, VEGF, PGDF, IL-1Ra, IL-8, MIP-1β, sFas, Fas-L, sTNF-R2, and sTNF-R1 as biomarkers for the severity of malaria. In another aspect, the present application discloses a method for determining the severity of malaria and predicting mortality due to cerebral malaria. The method comprises the detection of the biomarkers CXCL4 and/or CXCL10 and at least one more biomarker and determining the severity of malaria and predicting mortality due to cerebral malaria based upon the ratio of expression of the biomarkers in the subject versus the expression of the biomarkers in a control.

12 Claims, 4 Drawing Sheets

(56) References Cited

OTHER PUBLICATIONS

Yoshida et al.. "XBP1 mRNA is Induced by ATF6 and Spliced by IRE1 in Response to ER Stress to Produce a Highly Active Transcription Factor", Cell, vol. 107, pp. 881-891, Dec. 28, 2001.

Gunn et al.. "A role for the unfolded protein response in optimizing antibody secretion", Molecular Immunology, 2004, pp. 919-927, vol. 41.

Muller, M., et al., "Review: The chemokine receptor CXCR3 and its ligands CXCL9, CXCL10 and CXCL11 in neuroimmunity-a tale of conflict and conundrum", Neuropathology and Applied Neurobiology, 2010, pp. 368-387, vol. 36-Issue 5.

Srivastava, K., et al., "Platelet Factor 4 Mediates Inflammation in Cerebral Malaria", Cell Host Microbe., 2008, pp. 179-187, vol. 4-Issue 2.

Awandare, "Role of Macrophage Migration Inhibitory Factor (NIF) and MIF Promoter Polymorphisms in the Pathogenesis of Severe Malarial Anemia", PhD Dissertation, University of Pittsburgh Grad School of Public Health, 2007.

Griffith, K.S., et al., "Treatment of Malaria in the United States, A Systematic Review", JAMA, 2007, vol. 297, Issue 20, pp. 2264-2277.

Srivastava, K. et al. "Platelet Factor 4 Regulation of Monocyte KLF4 in Experimental Cerebral Malaria," PLoS One, May 2010, vol. 5, Issue 5, pp. 1-11.

Baptista, F.G. et al. "Accumulation of Plasmodium berghei-Infected Red Blood Cells in the Brain Is Crucial for the Development of Cerebral Malaria in Mice," Infection and Immunity, Sep. 2010, vol. 78, No. 9, p. 4033-4039.

* cited by examiner

COMPOSITIONS AND METHODS FOR DIAGNOSIS, PROGNOSIS AND MANAGEMENT OF MALARIA

This application is a Continuation of U.S. application Ser. No. 12/959,043, filed Dec. 2, 2010, which is a Continuation-In-Part of U.S. application Ser. No. 12/453,079, filed on Apr. 29, 2009. The entirety of the aforementioned applications is incorporated herein by reference.

FIELD

The present invention generally relates to compositions and methods for medical diagnosis and treatment. In particular, the compositions and methods of the present invention relate to the prognosis and management of malaria.

BACKGROUND

Malaria transmission and mortality rates remain unchanged in endemic countries lacking adequate health care and malaria control despite the use of preventive measures and treatments against malaria. A major obstacle to effective malaria control is the lack of affordable and accurate malaria diagnostics and treatment, which has led to misuse and abuse of anti-malarial drugs and the development of drug resistant parasites.

Microscopic examination of blood smears, the conventional method for *Plasmodium* detection, is currently being augmented with antigen- and PCR-based rapid diagnostic tests (RDTs) for blood. However, inaccurate microscopic evaluation of blood smears has resulted in misdiagnoses and misclassification of malaria severity. Blood taboos and increased risk of accidental infections due to needle pricks continue to impact malaria diagnosis negatively. In nonspecialized laboratories microscopic evaluation of blood smears is slow and may lead to delayed diagnoses and treatment, which contributes to high mortality rates.

Rapid diagnostic tests (RDTs) or "dipstick" tests are currently being used to detect antigens of *Plasmodium* species in blood or plasma to supplement microscopic evaluation of blood smears to manage tropical febrile disease. The benefits of this approach include rapid turnaround time and ease of use, which allows inexperienced laboratory or clinical staff to make on-the-spot diagnoses in the absence of visible parasites. However, issues associated with cultural objections to the collection of blood in communities with blood taboos and increased risk of needle injuries and disease transmission must be addressed.

In some patients *P. falciparum* infection can lead to a diffuse encephalopathy known as cerebral malaria (CM). CM is a serious complication of *P. falciparum* malaria with a wide range of associated neuropathological features. Despite treatment, mortality caused by CM can be as high as 30%, while 10% of survivors of the disease can experience short- and/or long-term neurological complications and cognitive dysfunction. Identification of reliable early predictors of CM severity will enable clinicians to adjust this risk with appropriate management of CM.

SUMMARY

One aspect of the present invention relates to a method for predicting the severity of malaria in an infected subject. In one embodiment, the method includes the steps of (a) measuring the level of CXCL4 in a sample from the subject, and (b) predicting the severity of malaria based on the level of CXCL4 in the sample.

In a related embodiment, the measuring step measures the level of CXCL4 and one or more other biomarkers in the sample from the subject, and the predicting step predicts the severity of malaria based on the levels of CXCL4 and the one or more other biomarkers.

In another related embodiment, the one or more other biomarkers are selected from the group consisting of CXCL10, vascular endothelial growth factor (VEGF), interlukin interleukin-1ra (IL-1ra), interleukin-8 (IL-8), macrophage inflammatory protein 1β (MIP-1β), soluble Fas (sFas), Fas ligand (Fas-L), soluble tumor necrosis factor receptor 1 (sTNF-R1), soluble tumor necrosis factor receptor 2 (sTNF-R2), platelet-derived growth factor with two B chains (PDGFbb) and macrophage migration inhibitory factor (MIF).

In another related embodiment, the one or more other biomarkers comprises CXCL10.

In another related embodiment, the one or more other biomarkers comprises MIF.

In another related embodiment, the one or more other biomarkers comprises sTNF-R2.

In another related embodiment, the one or more other biomarkers comprises sFas.

In another related embodiment, the one or more other biomarkers comprises PDGFbb.

In another related embodiment, the one or more other biomarkers comprises CXCL10 and one of VEGF, IL-1Ra, IL-8, MIP-1β, sFas, Fas-L, sTNF-R1, sTNF-R2, PDGFbb and MIF.

In another related embodiment, the one or more other biomarkers comprises CXCL10 and PDGFbb.

In another related embodiment, the one or more other biomarkers comprises CXCL10 and MIF.

In another related embodiment, the one or more other biomarkers comprises CXCL10 and sTNF-R2.

In another related embodiment, the one or more other biomarkers comprises CXCL10 and sFas.

In another related embodiment, the predicting step comprises comparing the expression level of CXCL4 to a predetermined threshold value, and determining the severity of malaria in the subject based on the result of the comparing step.

In another related embodiment, the predicting step comprises comparing the expression levels of CXCL4 and one or more other biomarkers to predetermined threshold values, and determining the severity of malaria in the subject based on the result of the comparing step.

In another related embodiment, the predicting step comprises comparing the expression levels of CXCL4 and one or more other biomarkers to predetermined threshold values, and determining the severity of malaria in the subject based on the result of the comparing step.

In another related embodiment, the predicting step comprises determining an expression ratio between two biomarkers, comparing the expression ratio to predetermined threshold values, and determining the severity of malaria in the subject based on the result of the comparing step.

Also disclosed is a method for diagnosing malaria. The method includes (a) detecting a presence of *Plasmodium* parasite in a first sample of the subject, wherein a detectable level of *Plasmodium* parasite in the first sample indicates malaria in the subject and wherein a subject with malaria is further subjected to the steps of: (b) measuring the level of one or more biomarkers in a second sample from the subject, and (c) predicting the severity of malaria based on the level of the one or more biomarkers in the sample.

In a related embodiment, the one or more biomarkers are selected from the group consisting of CXCL4, CXCL10, VEGF, IL-1Ra, IL-8, MIP-1β, sFas, Fas-L, sTNF-R1, sTNF-R2, PDGFbb and MIF.

In another related embodiment, the first sample is a saliva sample.

In another related embodiment, the first sample and the second sample are the same sample.

In another related embodiment, the first sample is a saliva sample and the second sample is a plasma sample, a serum sample or a cerebrospinal fluid sample.

Also disclosed is a method for monitoring a treatment for malaria. The method includes: (a) measuring the level of one or more biomarkers for malaria in a first sample harvested from the subject prior to the treatment, (b) measuring the level of the one or more biomarkers for malaria in a second sample harvested from the subject during or after the treatment, and (c) determining the effectiveness of the treatment based on the results of (a) and (b).

In a related embodiment, the one or more biomarkers are selected from the group consisting of CXCL4, CXCL10, VEGF, IL-1Ra, IL-8, MIP-1β, sFas, Fas-L, sTNF-R1, sTNF-R2, PDGFbb and MIF.

Another aspect of the present invention relates to a method for treating malaria in a subject. The method includes administering to the subject an effective amount of an agent that modulates the expression or activity of a malaria biomarker in the subject. In one embodiment, the agent is administered concurrently with a conventional treatment for malaria.

Another aspect of the present invention relates to kits for diagnosing and determining severity of malaria. In one embodiment, the kit comprises an antibody that binds specifically to an antigen of a *Plasmodium* species; an antibody that binds specifically to CXCL4; an antibody that binds specifically to CXCL10; an antibody that binds specifically to a malaria biomarker selected from the group consisting of VEGF, IL-1Ra, IL-8, MIP-1β, sFas, Fas-L, sTNF-R1, sTNF-R2, PDGFbb and MIF; and instructions on how to use the antibodies.

In a related embodiment, the antigen of a *Plasmodium* species is PfHRP II.

Also disclosed is a kit for predicting the severity of malaria in an infected subject a, comprising: an antibody that binds specifically to CXCL4; an antibody that binds specifically to CXCL10; an antibody that binds specifically to a malaria biomarker selected from the group consisting of VEGF, IL-1Ra, IL-8, MIP-1β, sFas, Fas-L, sTNF-R1, sTNF-R2, PDGFbb and MIF; and instructions on how to predict severity of malaria based on the levels of CXCL4, CXCL10 and other biomarkers.

Further objectives, features and advantages of the invention will be apparent from the following detailed description taken in conjunction with the accompanying drawings.

DETAILED DESCRIPTION

Figure 1A:
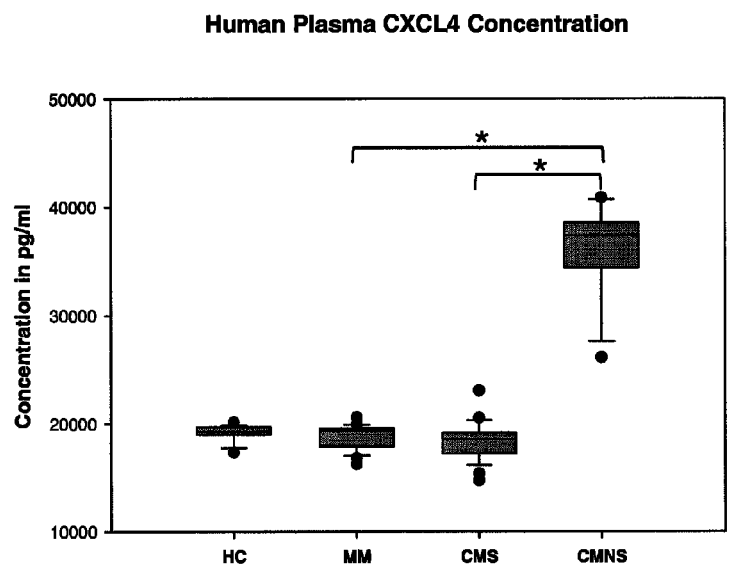
FIGS. 1A and 1B depict plasma levels of CXCL4 (FIG. 1A) and CXCL10 (FIG. 1B) in healthy controls (HC); mild malaria (MM); cerebral malaria survivor (CMS); and cerebral malaria non-survivor (CMNS). Box plot represent medians with 25th and 75th percentiles, bars for 10th and 90th percentiles, and points for outliers of CXCL4 and CXCL10 concentrations. Significant differences between CXCL4 and CXCL10 levels in different categories in relation to severity of CM were determined by Kruskal-Wallis One-Way ANOVA on Ranks using the Dunn's method to compare pairs of group. * represents p<0.05.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

One aspect of the present invention relates to a method of using one or more malaria biomarkers for predicting the severity of malaria in an infected subject or monitoring effectiveness of a treatment regimen.

In one embodiment, the method comprises the steps of (a) measuring the level of one or more biomarkers for malaria in a sample from the subject and (b) predicting the severity of malaria based on the level of the one or more other biomarkers in the sample.

In another embodiment, the method comprises the steps of (a) detecting a presence of *Plasmodium* parasite in a first sample of the subject, wherein a detectable level of *Plasmodium* parasite in the sample indicates malaria in the subject and wherein a subject with malaria is further subjected to the steps of: (b) measuring the level of one or more biomarkers in a second sample from the subject and (c) predicting the severity of malaria based on the level of the one or more biomarkers in the sample. In one embodiment, the first sample and the second sample are the same sample. In another embodiment, the first sample and the second sample are different samples form the same subject. For example, the first sample can be a saliva sample and the second sample can be a plasma sample or cerebrospinal fluid sample.

In yet another embodiment, the method comprises the steps of (a) measuring the level of one or more biomarkers for malaria in a first sample, wherein the first sample is harvested from the subject prior to the treatment, (b) measuring the level of the one or more biomarkers for malaria in a second sample, wherein the second sample is harvested from the subject during or after the treatment, and (c) determining the effectiveness of the treatment based on the results of (a) and (b).

Biomarkers for Malaria

A "biomarker" as used hereinafter, refers to a small molecule, protein, or nucleic acid that can be detected and measured in body fluids, or in samples obtained therefrom, whose presence or concentration reflects the presence, severity, type or progression of an infectious disease or parasitic infection in a subject. Said infectious disease or parasitic infection includes, but is not limited to, malaria, West Nile virus, HIV, and *Toxoplasma gondii*. More generally, a biomarker is anything that can be used as an indicator of a particular disease, disease state or other biological state of an organism. In molecular terms, biomarkers are the subset of markers that might be detected in a subject using genomics, proteomics or imaging technologies. A biomarker may include any of, but is not limited to, a cytokine, chemokine, growth factor, enzyme or a protein associated with an infectious disease or parasitic infection in the subject. A biomarker can also include a nucleic acid that encodes any of the above proteins or an mRNA or microRNA that is differentially expressed in a subject having an infectious disease or parasitic infection. A biomarker may be a substance whose presence is increased or decreased in a subject in concert with, or as a result of, an infectious disease or parasitic infection in the subject.

Biomarkers for malaria include, but are not limited to, IL-1β, IL-1Ra, IL-2, IL-4, IL-5, IL-6, IL-7, IL-8, IL-9, IL-10, IL-12 (p70), IL-13, IL-15, IL-17, Eotaxin, FGF basic protein, CRP, G-CSF, GM-CSF, TNF-γ, TNF-α, CXCL4, CXCL9, CXCL10, CXCL11, sFas, Fas-L, MCP-1 (MCAF), MIP-1α, MIP-1β, PANTES, SDF-1α, sTNF-R1 (p55), sTNF-R2 (p75), MMP-9, TGF-β1, VEGF, PGDFbb and MIF.

The preferred malaria biomarkers are CXCL4, CXCL10, VEGF, PGDFbb, IL-1Ra, IL-8, MIP-1β, sFas, Fas-L, sTNF-R2, sTNF-R1 and MIF.

CXCL4 (platelet factor 4 (PF4)) is a small cytokine that plays important roles in the control of immunity and inflammation as well as regulation of hematopoiesis and angiogenesis. CXCL4 is released from alpha-granules of activated platelets during platelet aggregation, and promotes blood coagulation by moderating the effects of heparin-like molecules.

CXCL10 is another small cytokine secreted by several cell types in response to IFN-γ or TNF-α. These cell types include monocytes, endothelial cells and fibroblasts. CXCL10 has been attributed to several roles, such as chemoattraction for monocytes/macrophages, T cells, NK cells, dendritic cells and glial cells of the CNS, promotion of T cell adhesion to endothelial cells, antitumor activity, and inhibition of bone marrow colony formation and angiogenesis. Both CXCL4 and CXCL10 are ligands of CXCR3, a CXC receptor whose expression is up regulated during malaria infection (see e.g., Campanella, G. S. et al., *Proc. Natl. Acad. Sci. U.S.A* [2008] 105:4814-4819 and Hansen, D. S. et al., *J. Immunol.* [2007] 178:5779-5788). Other ligands of CXCR3 include CXCL9 (MIG) and CXCL11 (IP-9, I-TAC). CXCL10 has been associated with cerebral malaria (CM) mortality when compared to severe malarial anemia (SMA) and non-malarial (NM) deaths (Armah et al., *Malaria J.* 2007, 6:147 and Jain et al., Malaria J. 2008, 7:83).

VEGF (vascular endothelial growth factor) is a sub-family of growth factors that belong to the platelet-derived growth factor family of cystine-knot growth factors. They are important signaling proteins involved in both vasculogenesis (the de novo formation of the embryonic circulatory system) and angiogenesis (the growth of blood vessels from pre-existing vasculature).

PGDF (platelet-derived growth factor) is a dimeric cytokine comprising two a (PGDF αα) or β (PGDFββ) chains or both and is known to mediate its effects through activation of its receptor tyrosine kinase. PDGF has been proposed to play an important role in atherogenesis because it can stimulate a variety of different proatherogenic genes in smooth muscle cells (SMC) (2). PDGF can exhibit its cellular effects via activation of protein kinase C, mitogenactivated, protein kinase (MAPK), and phospholipase C.

IL-1Ra (interleukin-1 receptor antagonist) is a member of the interleukin 1 cytokine family. This protein inhibits the activities of interleukin 1α (IL1A) and interleukin 1β (IL1B), and modulates a variety of interleukin 1 related immune and inflammatory responses.

IL-8 (Interleukin-8) is a chemokine produced by macrophages and other cell types such as epithelial cells. IL-8's primary function is to recruit neutrophils to phagocytose antigens that trigger the antigen pattern toll-like receptors.

MIP-1α (Macrophage Inflammatory Protein α) belong to the family of chemotactic cytokines known as chemokines. MIP-1α is one of a major factor produced by macrophages after they are stimulated with bacterial endotoxins. MIP-1α activates human granulocytes (neutrophils, eosinophils and basophils) which can lead to acute neutrophilic inflammation. MIP-1α also induces the synthesis and release of other pro-inflammatory cytokines such as interleukin 1 (IL-1), IL-6 and TNF-α from fibroblasts and macrophages.

sFas (soluble Fas) and Fas-L (Fas ligand) play an important role in the initiation of apoptosis. The interaction between Fas and FasL results in the formation of the death-inducing signaling complex (DISC), which triggers the execution of apoptosis of the cell.

sTNF-R2, and sTNF-R1 are receptors for TNF. TNF is a cytokine produced mainly by activated macrophages, and is the major extrinsic mediator of binary hipaloptic apoptosis. The binding of TNF to TNF-R1 initiates the pathway that leads to caspase activation via the intermediate membrane proteins TNF receptor-associated death domain (TRADD) and Fas-associated death domain protein (FADD).

MIF (macrophage migration inhibitory factor) is a lymphokine that may be involved in cell-mediated immunity, immunoregulation, and inflammation. It has been speculated that MIF plays a role in the regulation of macrophage function in host defense through the suppression of anti-inflammatory effects of glucocorticoids.

In one embodiment, the one or more other biomarkers are ligands that bind biomarkers for malaria include, but are not limited to, CXCL4, CXCL10, VEGF, PGDFbb, IL-1Ra, IL-8, MIP-1β, sFas, Fas-L, TNF-R1, sTNF-R2, and MIF.

In another embodiment, the one or more other biomarkers comprise CXCL4.

In another embodiment, the one or more other biomarkers comprise CXCL4 and at least one of CXCL10, sTNF-R2, sFas, VEGF and PGDFbb.

In another embodiment, the one or more other biomarkers comprise CXCL4 and CXCL10.

In another embodiment, the one or more other biomarkers comprise CXCL4 and sTNF-R2.

In another embodiment, the one or more other biomarkers comprise CXCL4 and sFas.

In another embodiment, the one or more other biomarkers comprise CXCL4 and VEGF.

In another embodiment, the one or more other biomarkers comprise CXCL4 and MIF.

In another embodiment, the one or more other biomarkers comprise CXCL4, CXCL10 and PGDFbb.

In another embodiment, the one or more other biomarkers comprise CXCL4, CXCL10 and VEGF.

In another embodiment, the one or more other biomarkers comprise CXCL4, CXCL10 and sTNF-R2.

In another embodiment, the one or more other biomarkers comprise CXCL4, CXCL10 and sFas.

In another embodiment, the one or more other biomarkers comprise CXCL4, CXCL10 and MIF.

In another embodiment, the one or more other biomarkers comprise CXCL4, VEGF and sTNF-R2.

In another embodiment, the one or more other biomarkers comprise CXCL4, VEGF and sFas.

In another embodiment, the one or more other biomarkers comprise at least CXCL4, sTNF-R2 and sFas.

In another embodiment, the one or more other biomarkers comprise CXCL4, CXCL10, VEGF and sTNF-R2.

In another embodiment, the one or more other biomarkers comprise CXCL4, CXCL10, VEGF and sFas.

In another embodiment, the one or more other biomarkers comprise at least CXCL4, CXCL10, VEGF, sFas and sTNF-R2.

In another embodiment, the one or more other biomarkers comprise at least CXCL4. CXCL10, VEGF, sFas, sTNF-R2 and PGDFbb.

In another embodiment, the one or more other biomarkers comprise at least CXCL4. CXCL10, VEGF, sFas, sTNF-R2, MIF and PGDFbb.

The Sample

The sample can be a body fluid sample such as blood, plasma, serum, lymph fluid, cerebrospinal fluid, saliva, urine or mucous. Alternatively, the sample can be a tissue sample, such as a biopsy sample.

In one embodiment, the sample is plasma. In another embodiment, the sample is cerebrospinal fluid. In yet another embodiment, the sample is saliva.

Determining the Levels of Biomarkers

Levels of the one or more biomarkers in the sample can be determined using detection methods well known in the art. The levels can be measured at the polypeptide level or polynucleotide level. Useful assays include, but are not limited to, immunoassays, mass spectroscopy, PCR, DNA arrays, and restriction fragment length polymorphism (RFLP) analysis.

Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

Also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (MA), Enzyme-Linked Immunosorbent Assay (ELISA), Flow cytometry, protein array, multiplexed bead assay, and magnetic capture.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner. Antibody arrays are available commercially. In addition to the conventional antibodies, Fab and scFv fragments, single V-domains from camelids or engineered human equivalents (Domantis, Waltham, Mass.) may also be useful in arrays.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which can be used diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumor extracts, and SELDI-TOF mass spectrometry is used to detection the retained proteins.

Other useful methodology includes large-scale functional chips constructed by immobilizing large numbers of purified proteins on a chip, and multiplexed bead assays.

DNA Arrays

A DNA or oligonucleotide microarray consists of an arrayed series of a plurality of microscopic spots of oligonucleotides, called features, each containing a small amount (typically in the range of picomoles) of a specific oligonucleotide sequence. The specific oligonucleotide sequence can be a short section of a gene or other oligonucleotide element that are used as probes to hybridize a cDNA or cRNA sample under high-stringency conditions. Probe-target hybridization is usually detected and quantified by fluorescence-based detection of fluorophore-labeled targets to determine relative abundance of nucleic acid sequences in the target.

The probes are typically attached to a solid surface by a covalent bond to a chemical matrix (via epoxy-silane, amino-silane, lysine, polyacrylamide or others). The solid surface can be glass or a silicon chip or microscopic beads. Oligonucleotide arrays are different from other types of microarray only in that they either measure nucleotides or use oligonucleotide as part of its detection system.

To detect gene expression in target tissue or cells using an oligonucleotide array, nucleic acid of interest is purified from the target tissue or cells. The nucleotide can be all RNA for expression profiling, DNA for comparative hybridization, or DNA/RNA bound to a particular protein which is immunoprecipitated (ChIP-on-chip) for epigenetic or regulation studies.

In one embodiment, total RNA is isolated (total as it is nuclear and cytoplasmic) by guanidinium thiocyanate-phenol-chloroform extraction (e.g. Trizol). The purified RNA may be analyzed for quality (e.g., by capillary electrophoresis) and quantity (e.g., by using a nanodrop spectrometer. The total RNA is RNA is reverse transcribed into DNA with either polyT primers or random primers. The DNA products may be optionally amplified by PCR. A label is added to the amplification product either in the RT step or in an additional step after amplification if present. The label can be a fluorescent label or radioactive labels. The labeled DNA products are then hybridized to the microarray. The microarray is then washed and scanned. The expression level of the gene of interest is determined based on the hybridization result using method well known in the art.

Detection of *Plasmodium* Parasite

Five species of the *Plasmodium* parasite can infect humans: the most serious forms of the disease are caused by *Plasmodium falciparum* and *Plasmodium vivax*. Malaria caused by *Plasmodium ovale* and *Plasmodium malariae* causes milder disease in humans that is not generally fatal. A fifth species, *Plasmodium knowlesi*, is a zoonosis that causes malaria in macaques but can also infect humans.

In one embodiment, the *Plasmodium* parasite is detected directly by microscopic examination of blood smears.

In another embodiment, the *Plasmodium* parasite is detected by the detection of *Plasmodium*-associated polynucleotides, such as *Plasmodium* DNA or RNA, by PCR-based assays.

In another embodiment, *Plasmodium* parasite is detected by the detection of *Plasmodium*-associated polypeptides, such as *Plasmodium* antigen or anti-*Plasmodium* antibodies by immuno-based assays (e.g., ELISA).

In one embodiment, the detection method detects a polynucleotide or a polypeptide associated with *P. falciparum*.

In another embodiment, the detection method detects the histidine-rich protein II of *P. falciparum* (PfHRP II antigen).

In yet another embodiment, the detection method detects the histidine-rich protein II of *P. falciparum* (PfHRP II antigen) in a saliva sample.

Predicting/Determining the Severity of Malaria

The severity of malarial infection may vary from asymptomatic infection to infection with mild symptoms, such as fever, to infection with severe symptoms, such as metabolic acidosis, severe anaemia, cerebral malaria, and to severe cerebral malaria that is likely to be fatal. An early diagnosis of malarial infection and early prediction or determination of the severity of the infection may improve the treatment outcome in malaria patient and reduce malaria-associated mortality.

The expression level (e.g., the amount of biomarkers detected in samples collected from infected individuals) of individual malaria biomarkers and ratios of between certain biomarkers in a sample or samples obtained from a subject can be used to diagnose the presence and/or severity of malaria infection in the subject. Alternatively, the expression level of individual malaria biomarkers and ratios of certain biomarkers in a sample or samples obtained from a subject can be used as a predictor of mortality of a subject.

In certain embodiments, the expression levels of one or more malaria biomarkers in a test subject are used to determine the presence and/or severity of malaria infection or to predict the mortality of malaria in the subject by comparing the expression level to a predetermined threshold value or threshold range. The threshold value or threshold range may be derived from the average expression level of the biomarker in uninfected healthy controls or the average expression level of the biomarker in control groups with malaria of different severity (e.g., group with mile malaria, group with cerebral malaria and group with lethal cerebral malaria). The threshold value or threshold range may vary based on race, age, gender, health conditions and geographic location of the test subject.

In one embodiment, a plasma CXCL4 concentration of 25 ng/ml or greater is indicative of severe cerebral malaria that is likely to be fatal.

In another embodiment, a plasma CXCL10 concentration of 0.1 ng/ml or greater is indicative of mild malaria, a plasma CXCL10 concentration of 0.5 ng/ml or greater, or a CSF CXCL10 concentration of 20 pg/ml or greater is indicative of cerebral malaria, and a plasma CXCL10 concentration of 1 ng/ml or greater is indicative of severe cerebral malaria that is likely to be fatal.

In another embodiment, a plasma CXCL4 concentration of 25 ng/ml or greater and a plasma CXCL10 concentration of 1 ng/ml or greater is indicative of severe cerebral malaria that is likely to be fatal In another embodiment, a plasma CXCL4 concentration of 25 ng/ml or greater and a CSF CXCL10 concentration of 20 pg/ml or greater is indicative of severe cerebral malaria that is likely to be fatal.

In another embodiment, a plasma CXCL4 concentration of 25 ng/ml or greater and a log MIF (pg/ml) levels of 10.8 or greater is indicative of severe cerebral malaria that is likely to be fatal.

In another embodiment, a plasma CXCL4 concentration of 25 ng/ml or greater, a CSF CXCL10 concentration of 20 pg/ml or greater and a log MIF (pg/ml) levels of 10.8 or greater is indicative of severe cerebral malaria that is likely to be fatal.

In another embodiment, a plasma CXCL10 concentration of 0.1 ng/ml or greater and a CSF sTNF-R1 concentration of 0.5 ng/ml or greater is indicative of malaria, a plasma CXCL10 concentration of 0.5 ng/ml or greater and a CSF sTNF-R1 concentration of 2 ng/ml or greater is indicative of cerebral malaria.

In another embodiment, a plasma CXCL10 concentration of 0.1 ng/ml or greater and a CSF sTNF-R2 concentration of 5 ng/ml or greater is indicative of malaria, and a plasma CXCL10 concentration of 0.5 ng/ml or greater and a CSF sTNF-R2 concentration of 10 ng/ml or greater is indicative of cerebral malaria.

In another embodiment, a plasma CXCL10 concentration of 0.1 ng/ml or greater and a CSF PDGFbb concentration of 5 pg/ml or less is indicative of malaria, and a plasma CXCL10 concentration of 0.5 ng/ml or greater and a CSF PDGFbb concentration of 2 pg/ml or less is indicative of cerebral malaria.

In another embodiment, a plasma CXCL10 concentration of 0.5 ng/ml or greater and a CSF IL-8 concentration of 1 pg/ml or greater is indicative of cerebral malaria.

In other embodiments, the expression levels of one or more malaria biomarkers in a test subject are compared to levels of the corresponding malaria biomarkers in a control subject or control group in order to determine the presence and/or severity of malaria infection or to predict the mortality of malaria in the subject.

In one embodiment, an elevated level of CXCL4 in a test subject, compared to that of corresponding normal controls, is indicative of severe cerebral malaria that is likely to be fatal.

In another embodiment, an elevated level of CXCL4 in a test subject and an elevated level of MIF, compared to those of corresponding normal controls, is indicative of severe cerebral malaria that is likely to be fatal.

In another embodiment, an elevated level of CXCL10 in a test subject, compared to that of corresponding normal controls, is indicative of malaria.

In another embodiment, an elevated level of CXCL10 in a test subject, compared to that of corresponding mild malaria controls, is indicative of cerebral malaria.

In another embodiment, an elevated level of CXCL10 in a test subject, compared to that of corresponding cerebral malaria controls, is indicative of cerebral malaria that is likely to be fatal.

In another embodiment, an elevated level of CXCL4 in a test subject, compared to that of corresponding normal or malaria controls, and an elevated level of CXCL10 in a test subject, compared to that of corresponding cerebral malaria controls, is indicative of cerebral malaria that is likely to be fatal.

In another embodiment, an elevated level of CXCL10 and an elevated level of sTNF-R1 or sTNF-R2 in a subject, compared to that of corresponding normal controls, is indicative of malaria.

In another embodiment, an elevated level of CXCL10 and an elevated level of sTNF-R1 or sTNF-R2 in a subject, compared to that of corresponding malaria controls, is indicative of cerebral malaria.

In another embodiment, a reduced level of CSF PDGFbb concentration in a subject, compared to that of corresponding normal controls, is indicative of malaria.

In yet another embodiment, a reduced level of CSF PDGFbb concentration in a subject, compared to that of corresponding malaria controls, is indicative of cerebral malaria.

In another embodiment, a reduced level of CSF VEGF concentration in a subject, compared to that of corresponding normal controls, is indicative of malaria.

In another embodiment, a reduced level of CSF VEGF concentration in a subject, compared to that of corresponding normal controls, is indicative of cerebral malaria.

In other embodiments, the expression ratios between malaria biomarkers in a subject are used to determine the severity of malaria. In one embodiment, the expression ratio of two biomarkers is compared to a threshold value or threshold range and a determination of the severity of malaria is made based on the result of the comparison. The threshold value or threshold range may be derived from the average expression level of the biomarker in uninfected healthy controls or the average expression level of the biomarker in control groups with malaria of different severity (e.g., group with mile malaria, group with cerebral malaria and group with lethal cerebral malaria). The threshold value or threshold range may vary based on race, age, gender, health conditions and geographic location of the test subject.

In one embodiment, an elevated CXCR10-to-PDGFbb, CXCR10-to-VEGF, sTNF-R2-to-VEGF, STNF-R2-to-PDGFbb, sFas-to-VEGF and/or sFas-to-PDGFbb ratio in the CSF of a test subject, as compared to that of a healthy control group, a malaria control group or a cerebral malaria control group, is indicative of cerebral malaria that is likely to be fatal.

In other embodiments, the ratios between two, three, or more pairs of biomarkers are used to distinguish more severely afflicted subject versus a standard, a healthy control or a less severely afflicted subject.

A number of other factors may be considered in determining the severity of malaria. Examples of such factors include, but are not limited to, parasite factors such as drug resistance, multiplication rate, invasion pathways, cytoadherence, rosetting, antigenic polymorphism and malaria toxin; host factors such as immunity, proinflammatory cytokines, genetics, age and pregnancy; and geographic and social factors such as access to treatment, culture and economic factors, and transmission intensity.

In other embodiments, expression levels of one or more biomarkers in samples obtained before and after a treatment for malaria are used to evaluate the effectiveness of the treatment.

In one embodiment, expression levels of one or more biomarkers are used as a "read-out" for the effectiveness of a treatment for malaria.

In a embodiment, the present invention provides a method for monitoring the effectiveness of malaria treatment in a subject with an agent (e.g., an agonist, antagonist, peptidomimetic, protein, peptide, polynucleotide, small molecule, or other drug candidate identified by the screening assays described herein). The method includes the steps of (i) obtaining a pre-administration sample from a subject prior to administration of the agent; (ii) detecting the level of expression of a malaria biomarker protein or mRNA in the pre-administration sample; (iii) obtaining one or more post-administration samples from the subject; (iv) detecting the level of expression or activity of the malaria biomarker protein or mRNA in the post-administration samples; (v) comparing the level of expression or activity of the malaria biomarker protein or mRNA in the pre-administration sample with the malaria biomarker protein or mRNA the post administration sample or samples; and (vi) altering the administration of the agent to the subject accordingly. According to such an embodiment, the malaria biomarker expression or activity may be used as an indicator of the effectiveness of an agent, even in the absence of an observable phenotypic response.

Another aspect of the present invention relates to kits for diagnosing and determining severity of malaria. In one embodiment, the kit comprises an antibody that binds specifically to an antigen of a *Plasmodium* species; an antibody that binds specifically to CXCL4; an antibody that binds specifically to CXCL10; an antibody that binds specifically to a malaria biomarker selected from the group consisting of VEGF, IL-1Ra, IL-8, MIP-1β, sFas, Fas-L, sTNF-R1, sTNF-R2, PDGFbb and MIF; and instructions on how to use the antibodies. In a related embodiment, the antigen of a *Plasmodium* species is PfHRP II.

Also disclosed is a kit for predicting the severity of malaria in an infected subject a, comprising: an antibody that binds specifically to CXCL4; an antibody that binds specifically to CXCL10; an antibody that binds specifically to a malaria biomarker selected from the group consisting of VEGF, IL-1Ra, IL-8, MIP-1β, sFas, Fas-L, sTNF-R1, sTNF-R2, PDGFbb and MIF; and instructions on how to predict severity of malaria based on the levels of CXCL4, CXCL10 and other biomarkers.

Another aspect of the present invention relates to methods for treating malaria in a subject. The method comprises administering to the subject, an effective amount of an agent that modulates the expression or activity of a malaria biomarker in the subject. In one embodiment, the agent is administered concurrently wherein said agent is administering concurrently with a conventional treatment for malaria.

Conventional treatments for malaria include treatment with a number of anti-malaria drugs. These drugs include, but are not limited to, quinine and related agents, chloroquine, amodiaquine, pyrimethamine, proguanil, sulfonamides, mefloquine, atovaquone, primaquine, artemisinin and derivatives, halofantrine, doxycycline, and clindamycin. Uncomplicated malaria is typically treated with oral antimalarial drugs, while severe malaria requires the parenteral administration of antimalarial drugs.

In one embodiment, the biomarker is selected from the group consisting of IL-1Ra, IL-8, CXCL4, CXCL10, sFas, Fas-L, sTNF-R1 (p55), sTNF-R2 (p75), ☐VEGF, PDGFbb and MIF.

In another embodiment, the agent is an antagonist of IL-1Ra, IL-8, CXCL4, CXCL10, sFas, Fas-L, sTNF-R1 (p55), sTNF-R2 (p75), ☐ or MIF that inhibits the activity or expression of IL-1Ra, IL-8, CXCL4, CXCL10, sFas, Fas-L, sTNF-R1 (p55), sTNF-R2 (p75) or MIF, respectively.

In another embodiment, the agent is an agonist of PGDFbb as well as VEGF that enhances the activity or expression of PGDFbb and VEGF.

The Antogonist

In one embodiment, the antagonist is an antibody that binds to IL-1Ra, IL-8, CXCL4, CXCL10, sFas, Fas-L, sTNF-R1 (p55), sTNF-R2 (p75) or MIF and inhibits its activity. The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with, for example, CXCL4 or CXCL10. The antibodies can be tested for their desired activity using the in vitro assays described herein, or by analogous methods, after which their in vivo therapeutic and/or prophylactic activities are tested according to known clinical testing methods.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response. Methods for humanizing non-human antibodies are well known in the art.

In another embodiment, the antagonist of the disclosed methods can be a functional nucleic acid that inhibits expression of IL-1Ra, IL-8, CXCL4, CXCL10, sFas, sTNF-R1 (p55), sTNF-R2 (p75) or MIF. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes and triplex forming molecules, RNAi and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of a target biomarker or the genomic DNA of the target biomarker or they can interact with the polypeptide of the target biomarker. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant (Kd) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with Kd's from the target molecule of less than $10^{-12}$ M. It is preferred that the aptamers bind the target molecule with a Kd less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a Kd with the target molecule at least 10, 100, 1000, 10,000, or 100,000 fold lower than the Kd with a background binding molecule. It is preferred when doing the comparison for a polypeptide for example, that the background molecule be a different polypeptide.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, hairpin ribozymes, and tetrahymena ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a Kd less than $10^{-6}$, $10^{-8}$, $10^{-10}$, or $10^{-12}$.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells.

Gene expression can also be effectively silenced in a highly specific manner through RNA interference (RNAi). This silencing was originally observed with the addition of double stranded RNA (dsRNA). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends. In an ATP dependent step, the siRNAs become integrated into a multi-subunit protein complex, commonly known as the RNAi induced silencing complex (RISC), which guides the siRNAs to the target RNA sequence. At some point the siRNA duplex unwinds, and it appears that the antisense strand remains bound to RISC and directs degradation of the complementary mRNA sequence by a combination of endo and exonucleases. However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, a siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer. siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit. Disclosed herein are any siRNA designed as described above based on the sequences for the target biomarker.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed inflammatory mediators.

Besides functional nucleotides, the antagonist of a biomarker expression or biomarker activity can be any small molecule that interferes or inhibits the expression or activity of the biomarker.

The Agonist

The agonist of PGDFbb or VEGF enhances PGDFbb or VEGF expression or PGDFbb or VEGF activity. The agonist can be PGDFbb or VEGF protein itself or a variant of PGDFbb or VEGF. The agonist can be viral or non-viral vectors that express PGDFbb or VEGF protein. The agonist can be any small molecule that enhances the expression or activity of PGDFbb or VEGF.

The Delivery Systems

There are a number of methods and compositions which can be used to deliver the antagonist of IL-1Ra, IL-8, CXCL4, CXCL10, sFas, Fas-L, sTNF-R1 (p55), sTNF-R2 (p75) or MIF, or the agonists of PDGFbb or VEGF to a cell, either in vitro or in vivo. These methods and compositions can largely be broken down into two classes: nucleic acid based delivery systems and non-nucleic acid based delivery systems.

Nucleic Acid Based Delivery Systems

The antagonist/agonist of malaria biomarker expression or activity may be delivered to the target cells using nucleic acid based delivery systems, such as plasmids and viral vectors. As used herein, plasmid or viral vectors are agents that transport nucleic acids into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. Viral vectors can have higher transfection (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter.

Enhancer generally refers to a sequence of DNA that functions at no fixed distance from the transcription start site and can be either 5' or 3' to the transcription unit. Furthermore, enhancers can be within an intron as well as within the coding sequence. They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region will be active in all eukaryotic cell types even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types. For example, the glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

Non-Nucleic Acid Based Systems

The antagonist or agonist of malaria biomarkers may also be delivered to the target cells using non-nucleic acid based systems. For example, the antagonist or agonist can be delivered through electroporation, or through lipofection, or through calcium phosphate precipitation. The delivery mechanism chosen will depend in part on the type of cell targeted and whether the delivery is occurring for example in vivo or in vitro.

The non-nucleic acid based systems can comprise lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

Composition and Kits

Another aspect of the present invention relates to compositions and kits for treating malaria. The composition includes (1) at least one antagonist of IL-1Ra, IL-8, CXCL4, CXCL10, sFas, Fas-L, sTNF-R1 (p55), TNF-R2 (p75) and/or at least one agonist of PDGFbb or VEGF, and (2) a pharmaceutically acceptable carrier.

By "pharmaceutically acceptable" means a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

A composition disclosed herein may be administered in a number of ways depending on whether local or systemic treatment is desired, and on the area to be treated. For example, the compositions may be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

The exact amount of the compositions required will vary from subject to subject, depending on the species, age, weight and general condition of the subject, the severity of the allergic disorder being treated, the particular nucleic acid or vector used, its mode of administration and the like. An appropriate amount can be determined by one of ordinary skill in the part using only routine experimentation given the teachings herein. Thus, effective dosages and schedules for administering the compositions may be determined empirically, and making such determinations is within the skill in the art. The dosage ranges for the administration of the compositions are those large enough to produce the desired effect in which the symptoms disorders are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

The materials described above as well as other materials can be packaged together in any suitable combination as a kit useful for performing, or aiding in the performance of, the disclosed method. It is useful if the kit components in a given kit are designed and adapted for use together in the disclosed method. In one embodiment, the kit contains a peptide or an antibody that specifically bind IL-1Ra, IL-8, CXCL4, CXCL10, sFas, Fas-L, sTNF-R1 (p55), sTNF-R2 (p75) or MIF, and instructions on how to use such a peptide or antibody.

The present invention is further illustrated by the following example which should not be construed as limiting. The contents of all references, patents and published patent applications cited throughout this application are incorporated herein by reference.

Example 1

Detection of *Plasmodium falciparum* Parasites in Saliva

The studies described here were conducted at the Korle-Bu Teaching Hospital's Child Health Department, Accra, Ghana, after ethical approval by Morehouse School of Medicine and University of Ghana Medical School.

A study was conducted to detect the presence of the number of *Plasmodium falciparum* parasites in saliva and estimate their number by ELISA. The method comprised the steps of collecting a sample of saliva from an individual as described below, exposing the samples of saliva to a support treated with anti-*P. falciparum* monoclonal capture antibodies and, after washing, allowing the support with the saliva to incubate. Plates were then exposed to a solution that enhanced conjugation of the antibodies to *P. falciparum* and the *P. falciparum* proteins. Preferably, the plates with the conjugates are then washed before exposure to at least one indicator such as a chromogen or fluorogen which will render the conjugate subject to inspection by visual inspection or by spectrophotometer. The particular antibody used in the kits as provided is an antibody to the PfHRP II. However, other malaria parasite specific proteins may be used.

Malaria Antigen ELISA kits (CELISA, Cellabs, Australia) were used in accord with the instructions provided therewith. This kit measures HRP II production during growth and multiplication of *P. falciparum* at a specificity of 96% and sensitivity of 98% in whole blood or plasma and can detect *P. falciparum* parasites at a limit of detection of 0.001%; thus incubation periods with reagents were the same for plasma and saliva for the same patient. The plates provided with the kits are coated with anti-*P. falciparum* monoclonal capture antibodies. If the *P. falciparum* antigen is present, it will bind to the coating of the plate.

Saliva was obtained by syringe from the mouths of children who were believed to have been or were known to have been exposed to malaria. In order to obtain sufficient saliva, each child was allowed to chew on a piece of sugar free gum before collection of the sample. However, saliva production may be increased by other means such as by simply exposing the subject from whom saliva is to be obtained for testing to the odor of a well liked food.

Wash Buffer was prepared by adding 50 ml PBS-Tween to 950 ml distilled water. Each kit containing the supplies provided by Cellabs contains positive controls, negative controls, enzyme conjugate, conjugate diluents, substrate chromogen, substrate buffer and stopping solution.

Working strength conjugate is prepared by adding 5 μl conjugate concentrate provided with the kit to 995 μl conjugate diluent.

Working strength substrate is prepared by adding 50 μl of substrate chromogen to 950 μl substrate buffer, then mixing thoroughly. (Stability period is <30 minutes).

In accord with the instruction of the kit, 100 μl of the sample, positive control or negative control was pipetted into each well. The plates were covered and incubated for 1 hour at room temperature in a humid chamber. (During the last 10 minutes of the incubation period, the working strength conjugate is prepared in order that it be fresh.)

The wells were then washed in accord with the instructions on the kit. 100 μl working conjugate was added to each well and the product was again incubated as above for 1 hour. The wash step is repeated. Prepared fresh working substrate (100 μl) is added to each well. The plates are then incubated in the dark (covered) at room temperature for 15 minutes, after which 50 μl stop solution is added. The results are read visually or in a spectrophotometer. On visual reading, the positive control should be blue before and yellow after stopping. A spectrophotometer can also be used in accord with the teachings of the manufacturer's instruction.

Samples (plasma and saliva) from children (22 months to 16 years) reporting to the Child Health Department's diagnostic laboratory were retrospectively analyzed for this study. Malaria positive cases were confirmed by thick film slides. Parasitemia was evaluated on the number of parasites per field (+, 1-10 parasites/100 fields, ++, >10 parasites/100 fields, +++, 1-10 parasites/field, and ++++>10 parasites/field) and at least 100 fields/slide were examined to rule out any negative thick film slide. Thirty thick film positive children and 10 negative children were enrolled. Red blood cells (infected and uninfected) and plasma were separated using Vacutainer Cell Preparation Tubes (CPT) with Sodium Citrate (Becton Dickinson, USA). Saliva was collected in sterile containers and aliquoted into microcentrifuge tubes and stored at −20° C. Saliva samples were centrifuged for 3 min at 14,000 rpm and the supernatants were analyzed by ELISA. Both saliva and plasma samples from the same patient were analyzed on the same plate, date, and conditions for PfHRP II antigen levels. The plasma samples were tested at a 1:2 dilution and all samples were run in duplicates by ELISA according to instructions of the manufacturer. The incubation period for primary and secondary antibodies with the samples was 1 hr each in a humid chamber and 15 min for enzyme development (substrate) in the dark at room temperature. The minimum limit of detection (cut-off level) of the kit was determined according to manufacturer's instructions.

Of the 30 children testing positive for blood smear, 16 (53%) had detectable PfHRP II antigens in their plasma (Table 1). Thirteen (43%) patients of the 30 positive blood smears were PfHRP II positive for saliva samples (Table 1). All patients that were PfHRP II positive for saliva were also positive for plasma. Three patients (P006, P008, and P011) were PfHRP II positive in plasma but negative for saliva samples. Surprisingly, P006 had a mean OD reading (0.144) that is slightly below the cut-off level of 0.161 compared with the other 2 (P008 and PO11) PfHRP II negative saliva. This observation suggests that P006 may have PJHRP II in the saliva that is undetectable in the kit used for this study. The 10 negative blood smears were also negative for PfHRP II antigen in both plasma and saliva. In our study the minimum limit of detection (cut-off level) was an OD reading of 0.161, which was determined according to the manufacturer's instructions. In addition, all 13 saliva specimens had lower titers (OD, 0.166-0.427) of PfHRP II with a mean of 0.209±0.07. The sensitivity of PfHRP II detection test for plasma was 53% and 43% for saliva whereas specificity was 100% for both specimens when compared with blood smears.

and *P. falciparum* are prevalent in this area. *P. falciparum* transmission occurs primarily during the monsoon and post-monsoon seasons (July-January). Pregnant women and patients with other manifestation of severe disease such as respiratory distress without CM and non-CM related coma, were excluded from the study. Data relating to age, sex, and level of parasitemia as well as complications such as seizure and renal failure were obtained from medical records. It was not possible to include data on non-malaria deaths to relate specificity of mortalities to malaria alone. Recent analyses of CSF and serum in fatal Ghanaian CM cases revealed that the observations were not part of a generalized fatal cascade in

TABLE 1

| Sample ID | Age in months | Gender | Parasitemia (Microscopic Evaluation) | *P. falciparum* HRPIIAg ELISA test |  |  |  |
|---|---|---|---|---|---|---|---|
|  |  |  |  | Plasma OD (SD) | +/− | Saliva OD (SD) | +/− |
| P001 | 156 | F | ++ | 3.640 (0.214) | + | 0.180 (0.026) | + |
| P002 | 192 | M | + | 0.063 (0.003) | − | 0.118 (0.043) | − |
| P003 | 84 | M | ++ | 0.059 (0.004) | − | 0.095 (0.003) | − |
| P004 | 144 | F | + | 3.296 (0.047) | + | 0.167 (0.001) | + |
| P005 | 192 | M | ++ | 0.070 (0.003) | − | 0.061 (0.001) | − |
| P006 | 60 | M | ++ | 2.976 (1.174) | + | 0.144 (0.016) | − |
| P007 | 192 | F | ++ | 0.073 (0.001) | − | 0.087 (0.037) | − |
| P008 | 120 | M | ++ | 2.621 (0.023) | + | 0.064 (0.006) | − |
| P009 | 144 | F | ++ | 0.223 (0.011) | + | 0.257 (0.011) | + |
| P010 | 30 | F | +++ | 3.464 (0.165) | + | 0.427 (0.051) | + |
| P011 | 192 | M | ++ | 1.565 (0.013) | + | 0.062 (0.003) | − |
| P012 | 144 | F | ++++ | 3.625 (0.144) | + | 0.185 (0.011) | + |
| P013 | 152 | F | + | 2.809 (0.089) | + | 0.179 (0.008) | + |
| P014 | 192 | F | +++ | 3.672 (0.249) | + | 0.195 (0.023) | + |
| P015 | 168 | F | ++++ | 3.426 (0.172) | + | 0.191 (0.031) | + |
| P016 | 108 | F | ++ | 0.039 (0.001) | − | 0.021 (0.004) | − |
| P017 | 36 | M | − | 0.125 (0.001) | − | 0.097 (0.025) | − |
| P018 | 72 | M | − | 0.090 (0.018) | − | 0.058 (0.001) | − |
| P019 | 96 | F | − | 0.043 (0.006) | − | 0.034 (0.007) | − |
| P020 | 84 | M | ++ | 3.274 (0.061) | + | 0.251 (0.017) | + |
| C001 | 22 | F | + | 0.061 (0.001) | − | 0.064 (0.004) | − |
| C002 | 72 | F | + | 0.054 (0.005) | − | 0.049 (0.003) | − |
| C003 | 44 | M | ++++ | 3.438 (0.165) | + | 0.176 (0.010) | + |
| C004 | 96 | F | + | 0.060 (0.001) | − | 0.063 (0.001) | − |
| C005 | 48 | M | + | 0.061 (0.001) | − | 0.061 (0.001) | − |
| C006 | 72 | F | ++ | 0.087 (0.005) | − | 0.076 (0.001) | − |
| C007 | 72 | F | ++ | 3.099 (0.041) | + | 0.169 (0.008) | + |
| C008 | 96 | F | + | 0.061 (0.001) | − | 0.077 (0.026) | − |
| C009 | 108 | F | ++++ | 3.201 (0.103) | + | 0.168 (0.004) | + |
| C010 | 23 | F | + | 0.061 (0.002) | − | 0.073 (0.001) | − |
| C011 | 192 | M | − | 0.058 (0.001) | − | 0.063 (0.003) | − |
| C012 | 180 | F | − | 0.065 (0.006) | − | 0.050 (0.004) | − |
| C013 | 22 | F | − | 0.064 (0.003) | − | 0.088 (0.006) | − |
| C014 | 48 | M | + | 0.062 (0.001) | − | 0.063 (0.001) | − |
| C015 | 48 | M | ++++ | 3.392 (0.157) | + | 0.166 (0.015) | + |
| C016 | 48 | F | +++ | 0.065 (0.003) | − | 0.053 (0.001) | − |
| C017 | 82 | M | − | 0.024 (0.006) | − | 0.014 (0.006) | − |
| C018 | 24 | M | − | 0.057 (0.002) | − | 0.038 (0.003) | − |
| C019 | 132 | F | − | 0.042 (0.004) | − | 0.029 (0.001) | − |
| C020 | 72 | M | − | 0.083 (0.014) | − | 0.047 (0.007) | − |

Example 2

Ratio of CXCR3 Ligands and Cytokines Compared to CM Survival

The study was conducted in a malaria-endemic region in Madhya Pradesh, India that accounts for 23% of all malaria cases in the state (Sharma, V. P., *Indian J. Med*. Res. [1996] 103:26-45). The study samples were obtained from two sites: Nethaji Subash Chandra Bose (NSCB) Hospital (a regional referral hospital) in Jabalpur and Civil Hospital (a primary hospital) in Maihar, Satna District. Both *Plasmodium vivax* human disease (Armah, H. B. et al., *Malar. J.* [2007] 6:147; Jain, V et al., *Malar. J.* [2008] 7:83, and Jain, V et al, *BMC Res Notes* [2009] 2:36).

Enrollment Criteria:

Cerebral Malaria:

All CM patients fulfilled the World Health Organization's (WHO) definition of CM (WHO, *Trans. R. Soc. Trop. Med. Hyg.* [2000] 94(Suppl. 1):S1-90), and had Glasgow coma score of ≤8, a *P. falciparum* parasitemia, and no other clinically evident cause of impaired consciousness Marsh, K. et al., *NEJM* [1995] 332:1399-1404). CM survivors (CMS) and non-survivors (CMNS) were separated into two separate groups. Non-survivors (CMNS) were enrolled if they died within three days of admission.

Mild Malaria:

Mild malaria patients had fever with *P. falciparum* parasitemia of <25,000 parasites/µl of blood (detected microscopically from blood smears) and no evidence of impaired consciousness, seizures, and no past history of mental illness, meningitis, or accidental head injury were included in this group.

Healthy Controls:

Relatives of patients in the hospital and members of the community who did not have malaria or other febrile illness were included after clinical evaluation.

Relevant clinical data and information (such as duration of coma and seizures) were recorded for each patient from physician's records (Jain, V. et al., *Malaria J.* [2008] 7:83; Jain, V. et al., *Am. J. Trop. Med. Hyg.* [2008] 79:636-642). Venous blood samples from children (2-5 ml) and adults (10 ml) were collected soon after enrolment into the study at the hospital from HC, MM, CMS, and CMNS groups prior to commencement of anti-malarial treatment or transfusions. Plasma was separated after centrifugation in Vacutainer Cell Preparation Tubes (CPT) containing Sodium Citrate (Becton Dickinson, USA), aliquoted and frozen at −80° C. for long-term storage.

Patient Characteristics:

The plasma samples from 16 HC, 26 MM, 26 CMS and 12 CMNS were selected randomly and analyzed. The characteristics of randomly selected subjects are described in Table 2. These subjects were selected as a subset of a prospective study conducted in India (Jain, V. et al., *Malaria J.* [2008] 7:83; Jain, V. et al., *Am. J. Trop. Med. Hyg.* [2008] 79:636-642). The main complications in CM patients but absent in HC and MM were seizure (CMS 46%, CMNS 67%) and renal failure (CMS 19%, CMNS 17%). Age, sex, and level of parasitemia did not affect prediction of the severity of malaria among the MM, CMS, and CMNS groups (Table 2). Anemia was present in all study groups, but the hemoglobin levels were significantly lower in the CMS ($p<0.005$) and CMNS ($p<0.001$) patients as compared to HC. Hemoglobin levels were significantly different between MM and CMNS ($p<0.05$) but not between MM and CMS groups.

CXCL9 (1.37-11.31 pg/mL), CXCL10 (0.41-4.46 pg/mL), and CXCL11 (3.4-39.7 pg/mL) (R&D Systems, MN). The results were interpolated from 5-parameter-fit standard curves generated using the relevant recombinant human proteins. Samples were tested at a 1:4 dilution.

Statistical Analysis:

Statistical analysis was performed with SigmaPlot 2006 (version 10.0) with SigmaStat (version 3.5) integration (Chicago, Ill.) software for windows. Data were analyzed by Kruskal-Wallis One-Way ANOVA on Ranks using the Dunn's method to compare pairs of group. A value of $P<0.05$ was considered significant. Receiver Operating Characteristic (ROC) curves enables the assessment of the ability of a test to discriminate between individual with and without disease (Altman, D. G. and Bland, J. M., *BMJ* [1994] 309:188). ROC curves were used to determine the predictive value of CXCR3 ligands among the different patient groups. The area under the ROC curve (AUC) is a reflection of how good a test can discriminate between patients with disease and those without disease (Akobeng, A. K., *Acta Paediatr.* [2007] 96:644-647). In general the closer the AUC is closer to 1 the better the overall diagnostic performance of the test, and the closer it is to 0.0 the poorer the test.

Figure 1B:
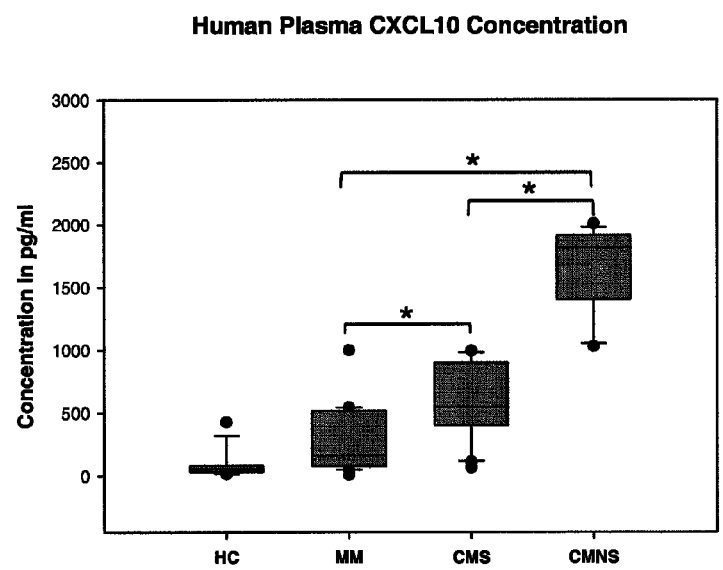
Figure 2A:
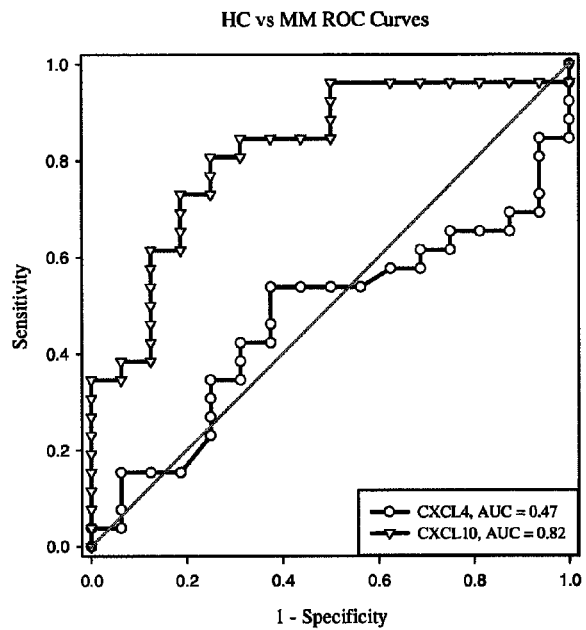
FIGS. 2A-2F depict receiver operating characteristic (ROC) curve analyses of CXCL4 and CXCL10 among the different patient groups. HC: healthy controls; MM: mild malaria; CMS: cerebral malaria survivor; and CMNS: cerebral malaria non-survivor. The diagonal line denotes an uninformative test, with an AUC of 0.5. A test with a perfect discrimination yields an AUC of 1. Sensitivity refers to the true positive rate and specificity refers to the true negative rate.
Figure 2B:
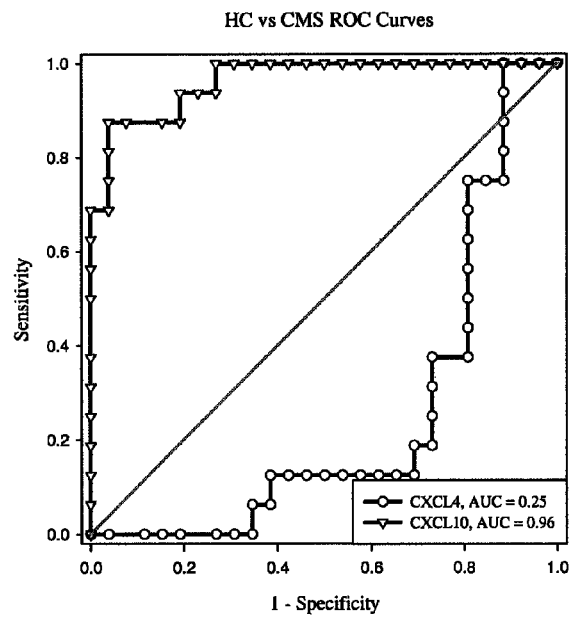
Figure 2C:
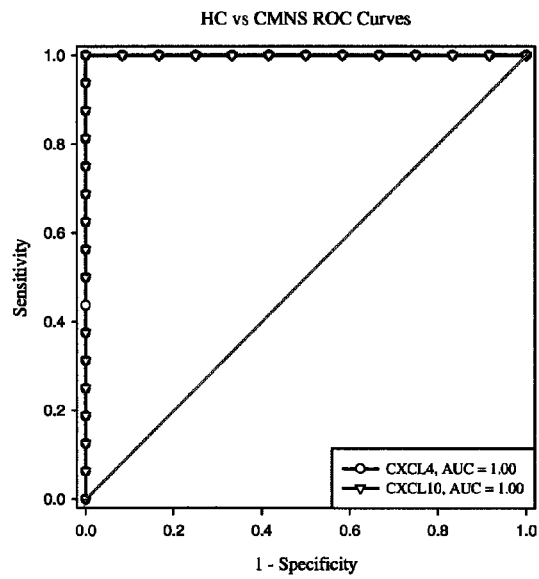
Figure 2D:
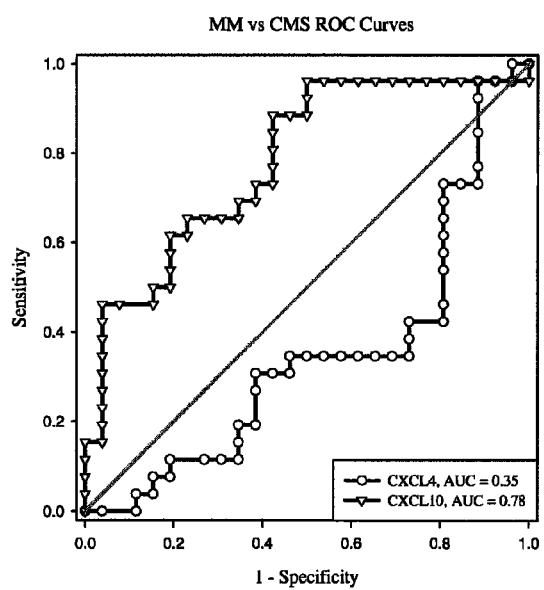
Figure 2E:
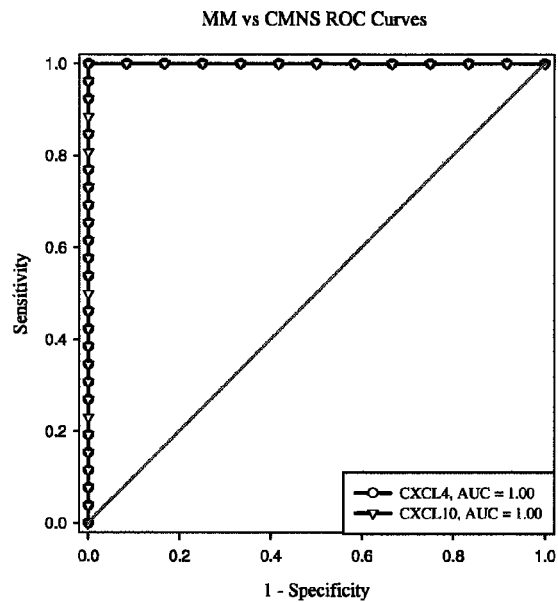
Figure 2F:
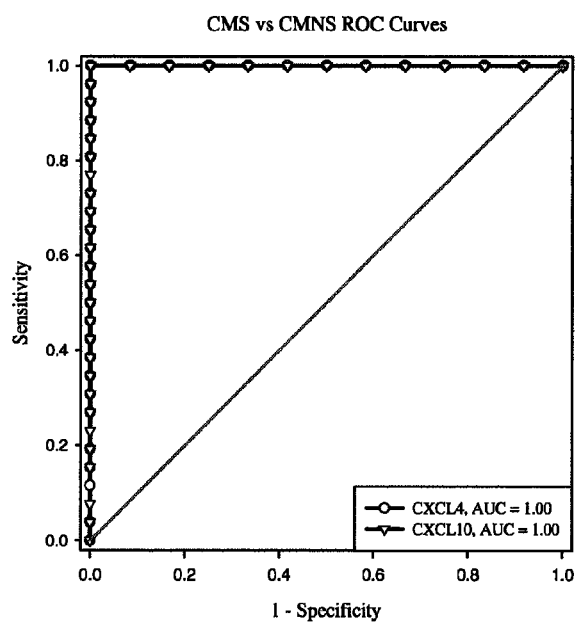

Plasma Levels of CXCR3 Ligands in HC, MM, CMS, and CMNS:

Pair wise comparisons were used to determine levels of significance of each ligand in the four groups (HC, MM, CMS, CMNS). CMNS patients had significantly higher plasma levels of the CXCL4 and CXCL10 compared to HC, MM, and CMS ($p<0.05$)(FIG. 1). However, plasma levels of CXCL11 and CXCL9 revealed no significant changes between MM, CMS, and CMNS (data not shown). None of these ligands could differentiate between MM and CMS except CXCL10 ($p<0.05$) (FIG. 1).

Receiver Operating Characteristic (ROC) Curve Analysis of CXCL4 and CXCL10 Levels in Patients Groups:

In order to determine specificity and sensitivity of CXCL4 and CXCL10, ROC curve analysis was used to determine the predictive value of the CXCL4 and CXCL10 among the groups (HC, MM, CMS, CMNS). Performing the pairwise ROC analysis, CXCL10 independently discriminated

TABLE 2

| CHARACTERISTIC | CATEGORY | | | |
| --- | --- | --- | --- | --- |
| | HC | MM | CMS | CMNS |
| Number of subjects | 16 | 26 | 26 | 12 |
| No. of males | 11 | 16 | 14 | 6 |
| No. of females | 5 | 10 | 12 | 6 |
| Mean age ± 2SD (yr) | 29.6 ± 5.2 | 23.3 ± 10.2 | 27.9 ± 12.4 | 20.0 ± 16.0 |
| Mean Glasgow Coma Score | 14 | 14 | 6.7 ± 2.5 | 5.2 ± 2.4 |
| Seizures | 0 | 0 | 12 | 8 |
| Geomean parasitemia ± 2SD (pRBC/mm3) | 0 | 863.4 ± 231.1 | 2256.6 ± 352.6 | 1336 ± 386.2 |
| Geomean hemoglobin ± 2SD (g/dL) | 10.6 ± 0.2 | 9.1 ± 1.5 | 7.8 ± 2.5 | 5.7 ± 2.0 |
| Renal failure | 0 | 0 | 5 | 2 |

Enzyme-Linked Immunosorbent Assay:

Plasma samples were evaluated for CXCL4, CXCL9, CXCL10, and CXCL11 by commercially available ELISA kits using human-specific primary and secondary antibodies. IMUCLONE Platelet Factor 4 ELISA was used for CXCL4 assay with minimum detectable limits of 0.5 ng/mL (American Diagnostica Inc, CT). The CXCL9, CXCL10 and CXCL11 assays were perform by using ELISA kits from R&D Systems with the following minimum detection limits;

between HC and MM with an AUC==0.82 and $p<0.001$ (FIG. 2 and Table 3). Both ligands (CXCL4 & CXCL10) could independently discriminate between HC and CMNS statistically with $p<0.0001$ and AUC=1 (FIG. 2 and Table 2). In addition, CXCL4 and CXCL10 could independently discriminate between MM and CMNS, and CMS and CMNS (FIG. 2 and Table 3). CXCL4 could not discriminate statistically between MM and CMS even though CXCL10 has a moderate AUC of 0.78 (FIG. 2 and Table 3).

TABLE 3

| Paired Groups | CXCL4 | | CXCL10 | |
|---|---|---|---|---|
| | AUC (95% CI) | P-value | AUC (95% CI) | P-value |
| HC vs MM | 0.47 (0.29-0.65) | 0.75 | 0.82 (0.69-0.95) | <0.001 |
| HC vs CMS | 0.25 (0.10-0.40) | 0.007 | 0.96 (0.92-1.00) | <0.0001 |
| HC vs CMNS | 1.00 (1.00-1.00) | <0.0001 | 1.00 (1.00-1.00) | <0.0001 |
| MM vs CMS | 0.35 (0.19-0.50) | 0.05 | 0.78 (0.65-0.91) | <0.001 |
| MM vs CMNS | 1.00 (1.00-1.00) | <0.0001 | 1.00 (1.00-1.00) | <0.0001 |
| CMS vs CMNS | 1.00 (1.00-1.00) | <0.0001 | 1.00 (1.00-1.00) | <0.0001 |

The above description is for the purpose of teaching the person of ordinary skill in the art how to practice the present invention, and it is not intended to detail all those obvious modifications and variations of it that will become apparent to the skilled worker upon reading the description. It is intended, however, that all such obvious modifications and variations be included within the scope of the present invention, which is defined by the following claims. The claims are intended to the components and steps in any sequence which is effective to meet the objectives there intended, unless the context specifically indicates the contrary. All the references cited above are herein incorporated by reference in their entirety.

What is claimed is:

1. A method for treating cerebral malaria in a human subject, comprising:
    administering to said subject an effective amount of an agent that modulates the expression or activity of a malaria biomarker in said subject,
    wherein said agent comprises an antagonist of IL-1Rα, IL-8, CXCL4, CXCL10, sFas, Fas-L, sTNF-R1 (p55) or sTNF-R2 (p75), and
    wherein said agent is administered concurrently with a conventional treatment for malaria.

2. The method of claim 1, wherein said agent comprises an antagonist of CXCL4 and an antagonist of CXCL10.

3. The method of claim 1, wherein said antagonist is an antibody that binds to IL-1Rα, IL-8, CXCL4, CXCL10, sFas, Fas-L, sTNF-R1 (p55), or sTNF-R2 (p75) and inhibits its activity.

4. The method of claim 1, wherein said antagonist is a functional nucleic acid that inhibits expression of IL-1Rα, IL-8, CXCL4, CXCL10, sFas, Fas-L, sTNF-R1 (p55), or sTNF-R2 (p75).

5. The method of claim 4, wherein said functional nucleic acid is selected from the group consisting antisense molecules, aptamers, ribozymes and triplex forming molecules, RNAi and external guide sequences.

6. The method of claim 4, wherein said antagonist comprises a plasmid containing the functional nucleic acid.

7. The method of claim 4, wherein said antagonist comprises a functional nucleic acid encoded in a viral vector.

8. The method of claim 1, wherein said antagonist is an antibody that binds to CXCL4 and inhibits its activity.

9. The method of claim 1, wherein said conventional treatment for malaria is treatment with an anti-malaria drug.

10. The method of claim 9, wherein said anti-malaria drug is selected from the group consisting of quinine and related agents, chloroquine, amodiaquine, pyrimethamine, proguanil, sulfonamides, mefloquine, atovaquone, primaquine, artemisinin and derivatives, halofantrine, doxycycline, and clindamycin.

11. The method of claim 1, wherein said conventional treatment for malaria is oral administration of an antimalarial drug.

12. The method of claim 1, wherein said conventional treatment for malaria is parenteral administration of an antimalarial drug.

* * * * *